US008346341B2

(12) United States Patent  
Greiser

(10) Patent No.: US 8,346,341 B2  
(45) Date of Patent: Jan. 1, 2013

(54) METHOD FOR DETERMINING AN ITEM OF POSITIONING INFORMATION FOR ECG ELECTRODES DURING AN EXAMINATION WITH A MAGNETIC RESONANCE FACILITY AND MAGNETIC RESONANCE FACILITY

(75) Inventor: Andreas Greiser, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 788 days.

(21) Appl. No.: 12/498,555

(22) Filed: Jul. 7, 2009

(65) Prior Publication Data

US 2010/0063381 A1 Mar. 11, 2010

(30) Foreign Application Priority Data

Jul. 9, 2008 (DE) .......................... 10 2008 032 343

(51) Int. Cl.
*A61B 5/05* (2006.01)
(52) U.S. Cl. .......................... 600/411; 600/410; 600/509
(58) Field of Classification Search .................. 600/407, 600/410, 411, 413, 414, 420, 424, 509
See application file for complete search history.

(56) References Cited

U.S. PATENT DOCUMENTS

| 8,036,734 | B2* | 10/2011 | Schmidt .................. 600/512 |
| 2004/0082870 | A1* | 4/2004 | Rudy et al. .............. 600/509 |
| 2005/0113665 | A1 | 5/2005 | Launay |
| 2007/0060829 | A1* | 3/2007 | Pappone .................. 600/509 |
| 2007/0164744 | A1* | 7/2007 | Kuhara et al. ........... 324/320 |
| 2009/0118610 | A1* | 5/2009 | Karmarkar et al. ..... 600/420 |
| 2009/0275805 | A1* | 11/2009 | Lane et al. .............. 600/300 |

FOREIGN PATENT DOCUMENTS

| DE | 4314743 A1 | 11/1993 |
| DE | 102004056591 A1 | 6/2005 |
| WO | WO 2004054434 A2 | 7/2004 |
| WO | WO 2007013994 A2 | 2/2007 |
| WO | WO 2007145562 A1 | 12/2007 |

* cited by examiner

*Primary Examiner* — Brian Casler
*Assistant Examiner* — Christopher Cook

(57) ABSTRACT

A method for determining an item of positioning information for ECG electrodes during an examination with a magnetic resonance facility is provided. An image data record of a region surrounding the heart of a patient and the electrodes arranged on the surface of the patient is recorded. A position of the longitudinal heart axis and a position of the electrodes in the image data record are determined. A target position suited to determining evaluable ECG signals is automatically calculated for each of the electrodes by considering the position of the longitudinal heart axis and a displacement from the position of the electrodes to the target position. An item of positioning information for the electrodes is displayed by taking the displacements into consideration.

17 Claims, 3 Drawing Sheets

METHOD FOR DETERMINING AN ITEM OF POSITIONING INFORMATION FOR ECG ELECTRODES DURING AN EXAMINATION WITH A MAGNETIC RESONANCE FACILITY AND MAGNETIC RESONANCE FACILITY

CROSS REFERENCE TO RELATED APPLICATIONS

This application claims priority of German application No. 10 2008 032 343.8 filed Jul. 9, 2008, which is incorporated by reference herein in its entirety.

FIELD OF THE INVENTION

The invention relates to a method for determining an item of positioning information for ECG electrodes during an examination with a magnetic resonance facility as well as a magnetic resonance facility.

BACKGROUND OF THE INVENTION

With functional examinations in particular, it is usual in modern magnetic resonance facilities to record the ECG of the patient in parallel with the magnetic resonance examination thereof. In addition to monitoring, gating processes can be controlled by means of these ECG signals for instance.

ECG electrode systems were thus developed especially for magnetic resonance facilities, said ECG electrode systems being easy to operate and robust and also allowing a reliable ECG derivation by reducing interfering influences as a result of movement or magnetic field effects.

The use of three ECG electrodes, which are attached ventrally very close to one another on the thorax, was proposed for instance. As a result of the minimal electrode distance, the sensitivity in terms of gradient or movement-induced effects thus reduces. Fiber optic cables which likewise prevent influences from magnetic fields are used in most cases for ECG signal derivation.

One problem however is and remains the positioning of the in particular three ECG electrodes such that an evaluable ECG signal is obtained, because the very close placement of the three ECG electrodes in respect of one another, as shown, significantly influences the quality of the derived ECG signal. If the electrodes are placed such that the heart axis draws an unfavorable angle in respect of the electrode pairs or if they are positioned on an unsuitable point relative to the heart for instance, the derived signals are frequently too weak or qualitatively unsuited to a stable evaluation of the ECG signal which is used particularly for triggering or gating purposes.

Nowadays it is thus usual for the electrode positions to be improved when a non-evaluable ECG signal is obtained, by repeatedly changing the attachment positions of the electrodes, according to a "trial and error" principle, until a satisfactory ECG signal can be detected.

SUMMARY OF THE INVENTION

The object underlying the invention is thus to specify a method, which, during a magnetic resonance examination, allows a rapid, reliable positioning of the ECG electrodes which can lead to an evaluable ECG signal.

To achieve this object, provision is made in accordance with the invention for a method for determining an item of positioning information for ECG electrodes during an examination with a magnetic resonance facility comprising the following steps:

recording an image data record of a region surrounding the heart of a patient and surrounding the electrodes already arranged on the surface of the patient, determining the position of the longitudinal heart axis in the data image record, determining the position of the electrodes in the data image record, automatically calculating for each of the electrodes a target position suited to determining evaluable ECG signals by taking the position of the longitudinal heart axis and a displacement from the position of the electrodes to the target position into account and displaying an item of positioning information for the electrodes by taking the displacements into account.

The present invention firstly provides for a systematic improvement in the individual electrode positioning. The underlying idea here is to obtain information relating to the current position of the initially roughly positioned ECG electrodes from an image data record, in order then to advantageously link it to information relating to the position of the heart which was obtained from the same image data record, such that information relating to an improved positioning can be obtained. The positioning information accordingly provides a specification and/or positioning instructions which indicates how the individual electrodes have to be moved in order to achieve an evaluable derivation of the ECG signal even after an additional positioning step.

This is advantageous in that an individually improved placement of the ECG electrodes is achieved for each patient. Time is thus saved in the majority of cases, since the time consuming approach by means of "trial and error" can be avoided. The systematic improvement in terms of positioning also dispenses with the use of alternative measuring programs (real-time imaging for instance) which compromise the image quality. The present invention finally achieves an ECG signal which can be evaluated in any case, so that the proportion of examinations with an image quality which is not suited to a diagnosis is reduced.

A localizer image data record can be recorded particularly advantageously as an image data record. These localizer image data records are already generally recorded by default in the workflow of the magnetic resonance heart examinations (Cardio MR), so that no additional recording of an image data record is necessary. Provision can be made here for a series of coronal localizer slices to be recorded.

In order to determine the position of the longitudinal heart axis, in other words the longitudinal axis through the left ventricle, this can be marked manually in the image data. An anatomically formed user thus obtains the image data record, in particular the localizer slices, and also identifies the position of the longitudinal heart axis on the basis of the position of the heart. He/she can then mark this in the image data by way of an input means.

Alternatively, it is preferably also possible for the position of the longitudinal heart axis to be determined on the basis of an automatic or semiautomatic segmentation of the heart. Semiautomatic and automatic segmentation methods, which determine the size, position and orientation of the heart and its parts, are already known sufficiently in the prior art. The use of such a method allows the geometry of the heart of the special patient to be determined and the position of the longitudinal heart axis to be easily derived therefrom.

The position of the ECG electrodes which were already placed on the patient beforehand can basically already be determined from a conventional image data record with the aid of corresponding image artifacts. Provision can however be particularly advantageously made for electrodes provided with magnetic resonance markers to be used. Such a magnetic resonance marker can be annular for instance and is usually filled with a liquid or substance which is clearly visible in the magnetic resonance recording. While the position of the electrodes in the image data record is frequently determined manually due to the poor contrast in the case of the non-use of magnetic resonance markers, in the method according to the invention it is also possible to automatically determine the position of the electrodes, particularly when using magnetic resonance markers which exhibit an easily determinable form for instance.

If both the geometry of the heart and also the position of the electrodes are automatically determined in this way, a completely automatic procedure is provided which no longer requires user intervention. A particularly advantageous configuration of the method according to the invention is then provided, which allows for a systematic, repeatable and improved positioning of the electrodes.

In a further configuration of the method according to the invention, a projection of the longitudinal heart axis and the positions of the electrodes on a coronal plane can be considered in order to calculate the target positions. The surface of the patient, to which the electrodes are attached, is basically an uneven hypersurface, which, as determined from the data of the image data record and within the scope of the method according to the invention for instance, can naturally also be used immediately as the basis for calculating the target positions. It is nevertheless apparent that the least computationally-intensive manner of using projections on a coronal plane likewise delivers surprising results.

Provision can now be made here for a rectangle, in particular a square, the diagonal of which forms the longitudinal heart axis, to be determined in order to determine the target position, the two vertices of the latter which are intersected by the diagonals and a further vertex being the target positions of the three electrodes. Particularly suitable target positions can be determined without any great computing effort for the determination of the ECG signals by way of such a simple geometric observation. Provision can be made here for the dimensions of the rectangle to be selected by taking the size of the heart, in particular of the distance between the heart valve plane and the cardiac apex into account. The rectangle ideally includes the complete projection of the heart on the coronal plane, so that a minimal distance between the electrodes is realized, evaluable ECG signals can however also be derived. The really easily determinable distance between the heart valve plane and the cardiac apex is used here in particular as a measure with which the side lengths of the rectangle can be scaled.

The positioning information can expediently be displayed as a coronal slice of the image data record which is overlayed with the positions and the target positions as well as the displacements. If the slice shows the heart itself for instance, the display of the positioning instruction on the monitor can at the same time show that the target positions are suitable. Provision can be made here in particular for the longitudinal heart axis and/or the rectangle used for calculation purposes and/or the positions of the electrons and/or the target positions and/or arrows, which symbolize the displacements and/or numerical specification for displacement paths and/or the exterior outlines of the current patient to be shown. An operator thus obtains all the information needed for a successful positioning of the ECG electrodes.

In addition to the method, the present invention also relates to a magnetic resonance facility, comprising a control unit and an ECG facility, with, in particular three ECG electrodes, which is characterized in that the ECG electrodes are provided with a magnetic resonance marker. Such a magnetic resonance facility is in particular surprisingly suited to implementing the method according to the invention in all described configurations with the aid of the control unit. The ECG electrodes which are advantageously provided with magnetic resonance markers allow the position thereof to be defined in as simple a manner as possible in the recorded data image record, whereupon, in addition to the advantageous application for the method according to the invention, it is also possible to monitor in subsequent image recordings whether the ECG electrodes were positioned meaningfully since both the heart and also the ECG electrodes are visible in a image data record.

In an advantageous further configuration, the markers may be circular or annular so that an effective distinction can be made between other features in the image data record, in particular an automatic localization of the electrodes.

BRIEF DESCRIPTION OF THE DRAWINGS

Further advantages and details of the present invention result from the exemplary embodiments described below as well as with reference to the drawings, in which.

DETAILED DESCRIPTION OF THE INVENTION

Figure 1:
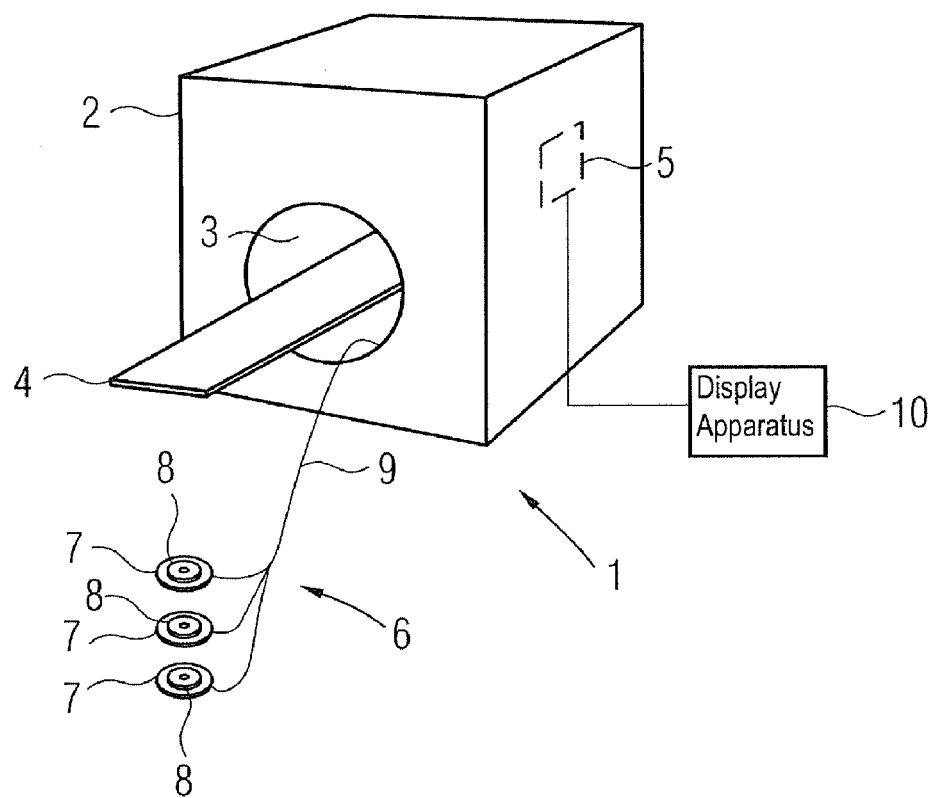
FIG. 1 shows an inventive magnetic resonance facility.

FIG. 1 shows an inventive magnetic resonance facility 1. It includes a magnet 2 with a patient receptacle 3, into which a patient couch 4 can be inserted. The magnetic resonance system 1 is controlled by way of a central control unit 5, which is embodied in order to implement the inventive method described below.

Furthermore, the magnetic resonance facility 1 includes an ECG facility 6 with three ECG electrodes 7 shown here enlarged, said ECG electrodes being provided in each instance with an annular magnetic resonance marker 8 and being attached ventrally to a patient to be examined in the region of the thorax. The ECG signals are derived here by way of electrical cables 9. They are used to trigger image recordings for instance.

As already indicated, the control unit 5 is embodied in order to implement the method according to the invention. To this end, coronal localizer slices are firstly recorded as an image data record, on which at least the heart and the electrodes 7 can be seen, illustrated here by the magnetic resonance marker 8. Information relating to the position of the longitudinal heart axis and the position of the electrodes 7 is not to be inferred from this localizer image data record, said information then being linked in order to determine the target positions suited to generating an evaluable ECG signal.

Provision is now made in order to determine the geometry of the heart and therefrom also the longitudinal axis of the left ventricle for the heart to firstly be segmented using a segmentation method known from the prior art, in order to determine therefrom the position of the longitudinal heart axis. Such segmentation methods are also known and need not be shown in more detail here. It is naturally just as easily possible for a user him/herself to manually determine the longitudinal heart axis in the image data record indicated on a display apparatus 10. Semiautomatic methods are also conceivable, in which Saat points or borders are specified for instance.

The positions of the ECG electrodes 7 are determined in the image data record beforehand, afterwards or at the same time. This is easily possible due to the magnetic resonance marker 8, in particular also in an automatic method. It is however also basically conceivable here for a manual marker to be performed.

Figure 2:
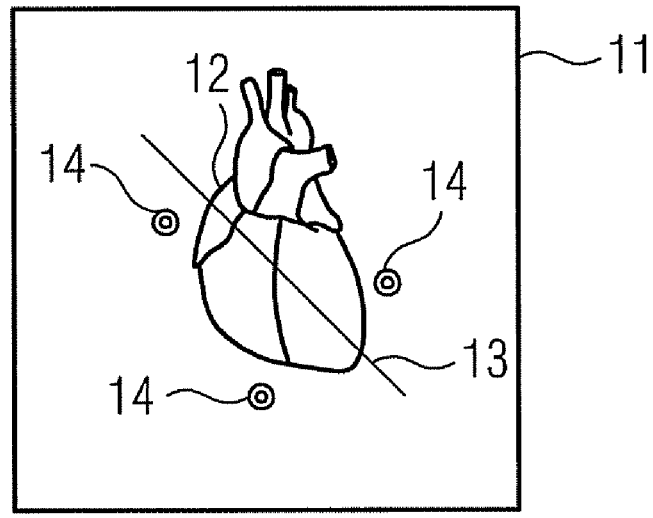
FIG. 2 shows a diagram for localizing the ECG electrodes relative to the longitudinal heart axis in an image data record.

Provision is firstly made in order to calculate the target positions for the determined positions and the position of the longitudinal heart axis to be projected onto a coronal plane, as is shown in more detail by FIG. 2. The projection 11 firstly shows the heart 12 and the longitudinal heart axis 13 leading therethrough. The positions 14 of the electrodes 7 can likewise be easily seen with the aid of the marker 8.

Figure 3:
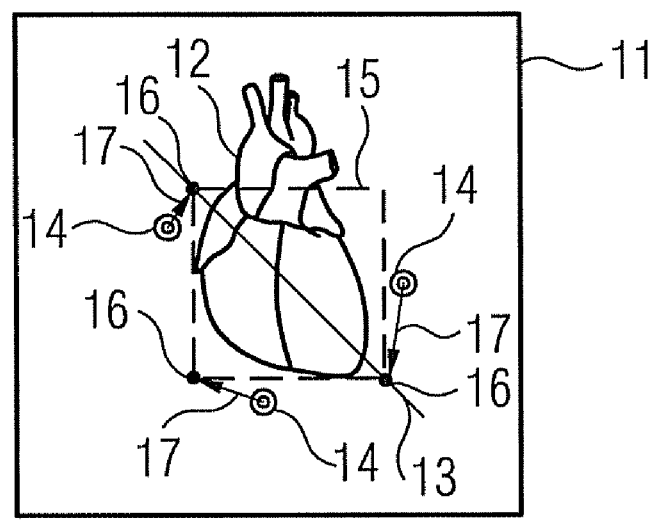
FIG. 3 shows the determination of target positions with the aid of the positions and the position of the longitudinal heart axis.

As shown in FIG. 3, a rectangle, in this case a square 15, the diagonal of which forms the longitudinal heart axis 13, is now firstly put inside the plane 11 in order to calculate the target position. The size of the square 15, in other words its lateral length, equates here to the distance between the heart valve plane and the cardiac apex and is thus selected by taking the size of the heart into consideration. The two vertices of the square 15, which are intersected by the longitudinal heart axis 13, and an additional vertex, result as the target positions 16. Based hereupon, the necessary displacements can now be determined for each of the electrodes 7, in other words based on the positions 14, which indicate in terms of amount and direction how the electrodes 7 have to be replaced in order to be fastened to the target positions 16. These displacements are shown in FIG. 3 by the arrow 17.

Figure 4:
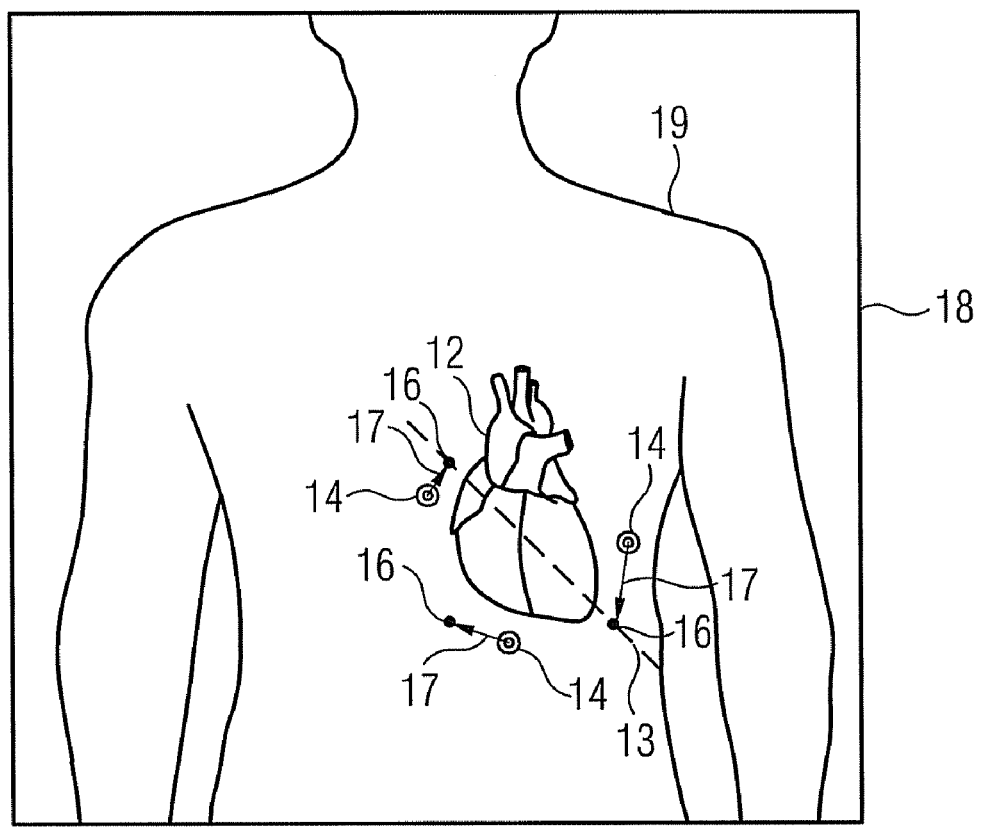
FIG. 4 shows a possible display of the positioning information.

A display, as shown in FIG. 3, can already be used to display the positioning information on the display facility 10. One further possibility of this is shown in FIG. 4. The positioning information, in particular the positions 14, the target positions 16 and the displacements 17 are displayed there overlaying a localizer slice 18, upon which, aside from the heart 12, the outlines 19 of the patient can be seen. The longitudinal heart axis 13 is also drawn in. It is also possible to fade the longitudinal specifications into the displacements 17.

In this way a user obtains, in particular automatically, all necessary positioning information, which is needed in order to improve the positioning of the electrodes 7, shown in a neat manner, and can achieve a useable positioning of the ECG electrodes 7 over a very short period of time and thus generate an evaluable ECG signal following on from the display of this information by means of the method according to the invention.

The invention claimed is:

1. A method for determining a positioning information for an electrocardiography (ECG) electrode of an ECG device during an examination with a magnetic resonance device, comprising:
   acquiring an image data record with the magnetic resonance device of a region surrounding a heart of a patient and surrounding the ECG electrode arranged on a surface of the patient;
   determining a position of a longitudinal heart axis in the image data record;
   determining a position of the ECG electrode in the image data record;
   calculating a target position for the ECG electrode suited to determining an evaluable ECG signal based on the position of the longitudinal heart axis and a displacement from the position of the ECG electrode to the target position; and
   displaying the positioning information for the ECG electrode comprising the position of the ECG electrode, the target position for the ECG electrode, and the displacement.

2. The method as claimed in claim 1, wherein the image data record is a localizer image data record.

3. The method as claimed in claim 1, wherein the position of the longitudinal heart axis is manually marked in the image data record.

4. The method as claimed in claim 1, wherein the position of the longitudinal heart axis is determined by an automatic or semiautomatic segmentation of the heart in the image data record.

5. The method as claimed in claim 1, wherein the position of the ECG electrode is determined manually or automatically.

6. The method as claimed in claim 1, wherein the target position is calculated automatically.

7. The method as claimed in claim 1, wherein the target position is calculated based on a projection of the longitudinal heart axis and the position of the ECG electrode on a coronal plane.

8. The method as claimed in claim 1, wherein the ECG electrode comprises a magnetic resonance marker.

9. The method as claimed in claim 1, further comprising determining a rectangle and wherein the longitudinal heart axis is a diagonal of the rectangle.

10. The method as claimed in claim 9, wherein the ECG device comprises three ECG electrodes and target positions of the three ECG electrodes are two vertices of the rectangle intersected by the diagonal and a further vertex.

11. The method as claimed in claim 9, wherein the longitudinal heart axis is a diagonal of a square.

12. The method as claimed in claim 9, wherein dimensions of the rectangle are selected based on a size of the heart.

13. The method as claimed in claim 12, wherein the size of the heart is measured by a distance between a heart valve plane and a cardiac apex.

14. The method as claimed in claim 1, wherein the positioning information is displayed in a coronal slice of the image data record which is overlaid with the position of the ECG electrode, the target position for the ECG electrode, and the displacement.

15. A magnetic resonance device, comprising:
   an electrocardiography (ECG), device comprising an ECG electrode arranged on a surface of a patient;
   an image recording device that records an image data record of a region surrounding a heart of a patient and surrounding the ECG electrode; and
   a control unit that:
      determines a position of a longitudinal heart axis in the image data record;
      determines a position of the ECG electrode in the image data record;
      calculates a target position for the ECG electrode suited to determining an evaluable ECG signal based on the position of the longitudinal heart axis and a displacement from the position of the ECG electrode to the target position; and
      displays the positioning information for the electrode comprising the position of the ECG electrode, the target position for the ECG electrode, and the displacement.

16. The magnetic resonance device as claimed in claim 15, wherein the ECG electrode comprises a magnetic resonance marker.

17. The magnetic resonance device as claimed in claim 16, wherein the marker is circular or annular.

* * * * *